United States Patent
Heriot

(10) Patent No.: US 10,688,296 B2
(45) Date of Patent: Jun. 23, 2020

(54) PRESSURE MANAGEMENT DEVICE

(71) Applicant: HERIOT EYECARE PTY. LTD., Melbourne, VIC (AU)

(72) Inventor: Wilson J. Heriot, Balwyn North (AU)

(73) Assignee: HERIOT EYECARE PTY. LTD., Melbourne (AU)

(*) Notice: Subject to any disclaimer, the term of this patent is extended or adjusted under 35 U.S.C. 154(b) by 19 days.

(21) Appl. No.: 16/066,007

(22) PCT Filed: Dec. 23, 2016

(86) PCT No.: PCT/AU2016/000406
§ 371 (c)(1),
(2) Date: Jun. 25, 2018

(87) PCT Pub. No.: WO2017/106901
PCT Pub. Date: Jun. 29, 2017

(65) Prior Publication Data
US 2019/0015656 A1    Jan. 17, 2019

(30) Foreign Application Priority Data

Dec. 24, 2015  (AU) .................................. 2015905389

(51) Int. Cl.
*A61M 39/28* (2006.01)
*A61F 9/007* (2006.01)
(Continued)

(52) U.S. Cl.
CPC .......... *A61M 39/28* (2013.01); *A61F 9/00781* (2013.01); *A61M 39/10* (2013.01);
(Continued)

(58) Field of Classification Search
CPC .... A61M 39/28; A61M 39/10; A61M 39/284; A61M 39/02; A61M 2039/282;
(Continued)

(56) References Cited

U.S. PATENT DOCUMENTS 4,337,774 A * 7/1982 Perlin .................. A61B 17/122
24/536
4,589,626 A    5/1986 Kurtz et al.
(Continued)

FOREIGN PATENT DOCUMENTS

| CA | 2602469 C | 3/2014 |
|----|-----------|--------|
| CN | 104984428 A | 10/2015 |
| EP | 0799627 A2 | 10/1997 |

OTHER PUBLICATIONS

International Preliminary Report on Patentability and Written Opinion dated Mar. 10, 2017 in counterpart PCT Application No. PCT/AU2016/000406.
(Continued)

*Primary Examiner* — Jessica Cahill
(74) *Attorney, Agent, or Firm* — Harness, Dickey & Pierce, P.L.C.

(57) ABSTRACT

A clip device for occluding two fluid lines and forming a fluid connection includes one of the fluid lines, the clip device including: a first clip segment including a fastener for engaging to a first fluid line, a first pinch valve for occluding the first fluid line and a coupling for connecting to the first fluid line; a second clip segment including a second pinch valve for occluding the second fluid line; and a bypass fluid line connectable or connected to the coupling. The second clip segment may also include a fastener for securing to the second fluid line. The first clip segment and/or the second clip segment may include a proximal opening and a distal opening through which the tubing passes. The proximal opening and the distal opening may be disposed on opposing sides of the segment.

19 Claims, 3 Drawing Sheets

(51) Int. Cl.
 *A61M 39/10* (2006.01)
 *A61M 39/02* (2006.01)

(52) U.S. Cl.
 CPC ........... *A61M 39/284* (2013.01); *A61M 39/02* (2013.01); *A61M 2039/282* (2013.01)

(58) Field of Classification Search
 CPC ........ A61F 9/00781; F16K 7/06; F16K 7/063; F16K 7/065; F16K 7/066; F16K 7/068
 USPC ........................... 251/6, 9–10; 606/157–158
 See application file for complete search history.

(56) References Cited

U.S. PATENT DOCUMENTS

| | | | | |
|---|---|---|---|---|
| 5,423,769 A * | 6/1995 | Jonkman | ............ | A61M 1/3664 604/250 |
| 5,910,110 A | 6/1999 | Bastable | | |
| 6,592,558 B2 * | 7/2003 | Quah | .................. | A61M 39/284 128/912 |
| 9,168,355 B2 * | 10/2015 | Braga | ................. | A61M 1/3661 |
| 10,082,241 B2 * | 9/2018 | Janway | ................. | A61M 39/28 |
| 10,398,836 B2 * | 9/2019 | Kato | .................... | A61M 39/284 |
| 2002/0087126 A1 | 7/2002 | Quah | | |
| 2002/0151838 A1 * | 10/2002 | Beck | ................. | A61M 5/14232 604/67 |
| 2004/0249334 A1 * | 12/2004 | Cull | .................... | A61M 1/3655 604/9 |
| 2005/0253390 A1 | 11/2005 | Blazek | | |
| 2006/0081797 A1 * | 4/2006 | Zerfas | ................. | A61M 39/284 251/10 |
| 2008/0082080 A1 * | 4/2008 | Braga | ................. | A61M 1/3661 604/523 |
| 2013/0267892 A1 * | 10/2013 | Woolford | ............ | A61M 3/0258 604/34 |
| 2017/0246444 A1 * | 8/2017 | Domatch | ............ | A61M 1/0062 |
| 2018/0274689 A1 * | 9/2018 | Gagne | ................... | F16K 27/003 |

OTHER PUBLICATIONS

European Search Report dated Aug. 7, 2019 in corresponding European Application No. 16876990.9.

* cited by examiner

PRESSURE MANAGEMENT DEVICE

CROSS-REFERENCE TO RELATED APPLICATIONS

This application is a National Phase Entry of International Patent Application No. PCT/AU2016/000406, filed on Dec. 23, 2016, which claims priority to Australian Patent Application Serial No. 2015905389, filed on Dec. 24, 2015, both of which are incorporated by reference herein.

TECHNICAL FIELD

The present invention relates to a pressure management device and method for occluding two fluid lines and forming a connection comprising one of the fluid lines. More particularly, this invention relates to a device and method for occluding both a fluid infusion line and an air line and forming a connection between the air line and an ocular line of an infusion tubing for an ocular surgical system.

BACKGROUND

A vitrectomy is surgery to remove some or all of the vitreous gel from the middle of the eye. It may be performed when there is a retinal detachment, because removing the vitreous gel gives better access to the back of the eye. The vitreous gel may also be removed if blood in the vitreous gel does not clear on its own.

After removing the vitreous gel, the surgeon may treat the retina with a laser (photocoagulation), cut or remove fibrous or scar tissue from the retina, flatten areas where the retina has become detached, or repair tears or holes in the retina or macula.

Vitreoretinal surgery is performed in a pressure controlled closed chamber where the infusion of either a balanced salt solution (BSS) or air is pressure regulated. The Alcon™ Constellation™ Vision System is one popular device for carrying our vitreoretinal surgery.

It is necessary to operate in a pressure controlled closed chamber to avoid globe collapse because the eye softens during the fluid aspiration that occurs with vitrectomy and scleral rigidity is required to move the eye and to allow easy instrument exchange. Initially, pressure was provided using gravity to move the BSS from the bottle through the infusion tubing into the eye. The Constellation™ Vision System provides integrated pressurized infusion pressurising BSS fluid in a disposable cassette, measuring the flow into the eye and integrating through the microprocessor of an integrated computer.

The infusion tubing of the Constellation™ Vision System includes an air infusion line which is linked to the BSS fluid infusion line but is protected by a duckbill valve to prevent fluid reflux into the airline to protect the delicate gas pressure controlling mechanism. In two important situations, the current infusion tubing design creates problems, one of which is unregulated and inconsistent pressure whilst the other is potentially very dangerous.

In the first and most common situation, for many procedures a long acting gas mixture is exchanged for the intra-operative gas by performing an "exchange transfusion" where the desired post-operative mixture is flushed through vitreous cavity progressively increasing the concentration from 0% to the desired final concentration (for example 30% SF 6). With the current infusion tubing, the intraocular pressure cannot be regulated during this step and many people allow gas to escape intermittently from an open sclerotomy or vent via a 30 gauge needle inserted via the pars plana relying on the resistance in the fine needle to regulate the pressure. This is problematic because this is venting to atmospheric pressure (0 mmHg) and not to the desired intraocular pressure of around 20 mmHg.

In the second situation, silicon oil is injected at very high pressure that can cause the eye to rupture because there is no feedback system regulating the intraocular pressure during the injection. This has caused rupture of the globe either through the sclera or, for example, corneal graft but can also cause other problems due to the high pressure and shutdown of the retinal circulation.

Indeed, duckbill valves of the current infusion tubing have been associated with infusion bubbles and uncontrolled reflux, which has prompted the repurposing of the duckbill valve with a one-way valve ("*Elimination of Infusion bubbles and uncontrolled reflux in the Alcon constellation vitrectomy vision system*" Russell, S. R., Sohn, E. H., Boldt, H. C., Folk, J. J., Tarantola, R. M., Kay, C. N., Mahajan, V. B., Retina: 2013; 33(4); 803-6).

The reference to any prior art in this specification is not, and should not be taken as, an acknowledgement or any form of suggestion that the prior art forms part of the common general knowledge.

SUMMARY

The present invention is directed to a device and a method for occluding two fluid lines and forming a connection comprising one of the fluid lines.

In a broad form the invention relates to a device that occludes both a fluid infusion line and an air line and forms a connection between the air line and an ocular line of an infusion tubing for an ocular surgical system.

In one form, although it need not be the only or indeed the broadest form, the invention resides in a clip device for occluding two fluid lines and forming a fluid connection comprising one of the fluid lines, the clip device comprising:
  a first clip segment comprising a fastener for engaging to a first fluid line, a first pinch valve for occluding the first fluid line and a coupling for connecting to the first fluid line;
  a second clip segment comprising a second pinch valve for occluding the second fluid line; and
  a bypass fluid line connectable or connected to the coupling.

The second clip segment may also comprise a fastener for securing to the second fluid line.

The first clip segment and/or the second clip segment may comprise a proximal opening and a distal opening through which the tubing passes. The proximal opening and the distal opening may be disposed on opposing sides of the segment.

The first clip segment may comprise a first tubing channel extending between the proximal opening and the distal opening. The first pinch valve may be disposed within the first tubing channel.

The second clip segment may comprise a second tubing channel extending between the proximal opening and the distal opening. The second pinch valve may be disposed within the second tubing channel.

The first clip segment may further comprise a bypass tube opening. The bypass tube opening may be disposed in or proximal to the rack.

In one embodiment, the first clip segment and the second clip segment are comprised on an integrated body. The integrated body may comprise a central spine. The central spine may extend between the first segment and the second segment. The central spine may extend between the first fluid line channel and the second fluid line channel.

The coupling may comprise a shaft comprising a sharp point to penetrate the first fluid line tubing wall. The coupling may further comprise a coupling attachment to connect the shaft to the bypass fluid line.

The clip may further comprise a coupling guide for positioning the coupling in an appropriate orientation to connect with the first fluid line.

The first clip segment, second clip segment and/or the integrated body may further comprise a ratchet for holding the clip closed. The ratchet may comprise a rack comprising one or more tooth, and a pawl.

The first clip segment, second clip segment and/or the integrated body may comprise a frame, the frame may comprise an exterior surface and an interior surface. The frame may further comprise a shoulder at a pawl end to aid operation of the ratchet. The frame may further comprise surface texture at the rack end which also aids user operation of the ratchet by providing some grip.

The frame may comprise a looped shape. The looped shape may comprise, at one side, a 180° curve between the two stems comprising the pinch valve. The 180° curve may provide the bias for the ratchet. The looped shape may further comprise a 90° curve between one stem and the pawl. When the ratchet is engaged or closed, the looped shape may comprise a continuous or closed loop and closed clip segment or integrated body may comprise a general obround shape. When the ratchet is disengaged or open, the looped shape may comprise an open loop.

The frame may further comprise thickened segments to construct the stems. The thickened segments may be comprised on the long sections of the frame.

The frame may be comprised of two long sections and two short sections. The stems may be disposed on the long sections. The proximal opening and the distal opening may be comprised or substantially comprised on the short sections.

The frame may define one or more of the first clip segment proximal opening, the first clip segment distal opening, the first tubing channel, the second clip segment proximal opening, the second clip segment distal opening, the second tubing channel, the first pinch valve, the second pinch valve, the one or more tooth, the shoulder and the surface texture.

The bypass fluid line may further comprise a stopcock or valve connection.

The clip device may be comprised of a surgical grade material.

The clip device may be comprised of surgical grade polymeric material or a surgical grade thermopolymeric material such as, one or more of a polyurethane; a polyamide; a fluoropolymer; a polyolefin; a polyvinylchloride, a polyimides; or a polyetheretherketone (PEEK).

The clip device may be disposable.

In a second form, the invention further provides a method for occluding two fluid lines and forming a connection comprising one of the fluid lines, the method comprising:

occluding a first fluid line with a first pinch valve disposed on a first clip segment;
occluding a second fluid line with a second pinch valve disposed on a second clip segment; and
connecting the first fluid line to a third fluid line with a bypass fluid line.

In one embodiment of the second form, the method comprises using the clip device of the first form.

In a third form the invention also provides a method of manufacturing a clip device for occluding two fluid lines and forming a fluid connection comprising one of the fluid lines, the method comprising:

forming a first clip segment comprising a fastener for engaging to a first fluid line, a first pinch valve for occluding the first fluid line and a coupling for connecting to the first fluid line;
forming a second clip segment comprising a second pinch valve for occluding the second fluid line; and
forming a bypass fluid line connectable or connected to the coupling.

Further aspects and/or features of the present invention will become apparent from the following detailed description.

BRIEF DESCRIPTION OF THE DRAWINGS

In order that the invention may be readily understood and put into practical effect, reference will now be made to embodiments of the present invention with reference to the accompanying drawings, wherein like reference numbers refer to identical elements. The drawings are provided by way of example only, wherein.

Figure 1:
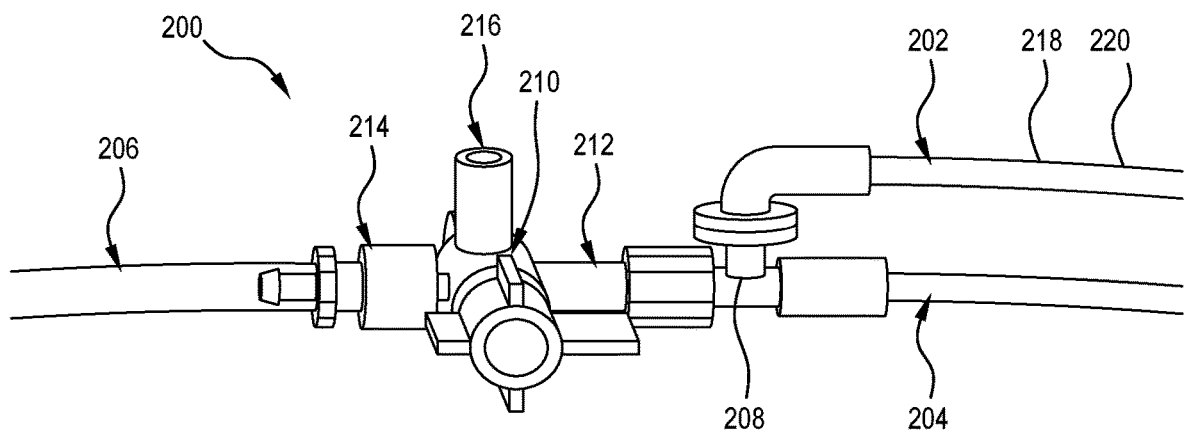
FIG. 1 shows the assembled infusion tubing used in the Constellation™ Vision System.

Skilled addressees will appreciate that elements in the drawings are illustrated for simplicity and clarity and have not necessarily been drawn to scale. For example, the relative dimensions of some elements in the drawings may be distorted to help improve understanding of embodiments of the present invention.

DETAILED DESCRIPTION

The present invention is directed to a device and a method for occluding two fluid lines and forming a connection comprising one of the fluid lines. In one application the invention provides a device that occludes both a fluid infusion line and an air line and forms a connection between the air line and an ocular line of an infusion tubing for an ocular surgical system.

This present invention has, in part, arisen from the present inventor's discovery that during vitrectomy, injecting a long acting gas into the closed chamber will elevate the intraocular pressure unless a venting outlet is provided. The optimal way to achieve this would be to allow the gas to ventilate back into the pressure controlled gas system to maintain the optimal intraocular pressure but, to achieve this in the Constellation™ Vision System, the present inventor has recognised, there must be a bypass of the duckbill valve.

The device of the invention is a novel and inventive solution that bypasses the "duckbill" valve prior to the injection of the post-operative gas or silicon oil. To ensure that no fluid is returned to damage the Constellation™ Vision System pressure regulation mechanism, it is obligatory to close the BSS infusion line simultaneously with the opening of the bypass fluid line.

FIG. 1 shows assembled infusion tubing 200 ready for use with the Constellation™ Vision System. The first fluid line 202, which is an air line, can be seen to be connected to the second fluid line 204, which carries BSS, via the duckbill valve 208. This part of the tubing is connected to the third fluid line 206 via the stopcock 210. Using the eye as a point of orientation, the first and second fluid lines 202, 204 are connected to stopcock 210 through a distal attachment 212 and the third fluid line 206 is connected to the stopcock 210 through proximal attachment 214.

Figure 2:
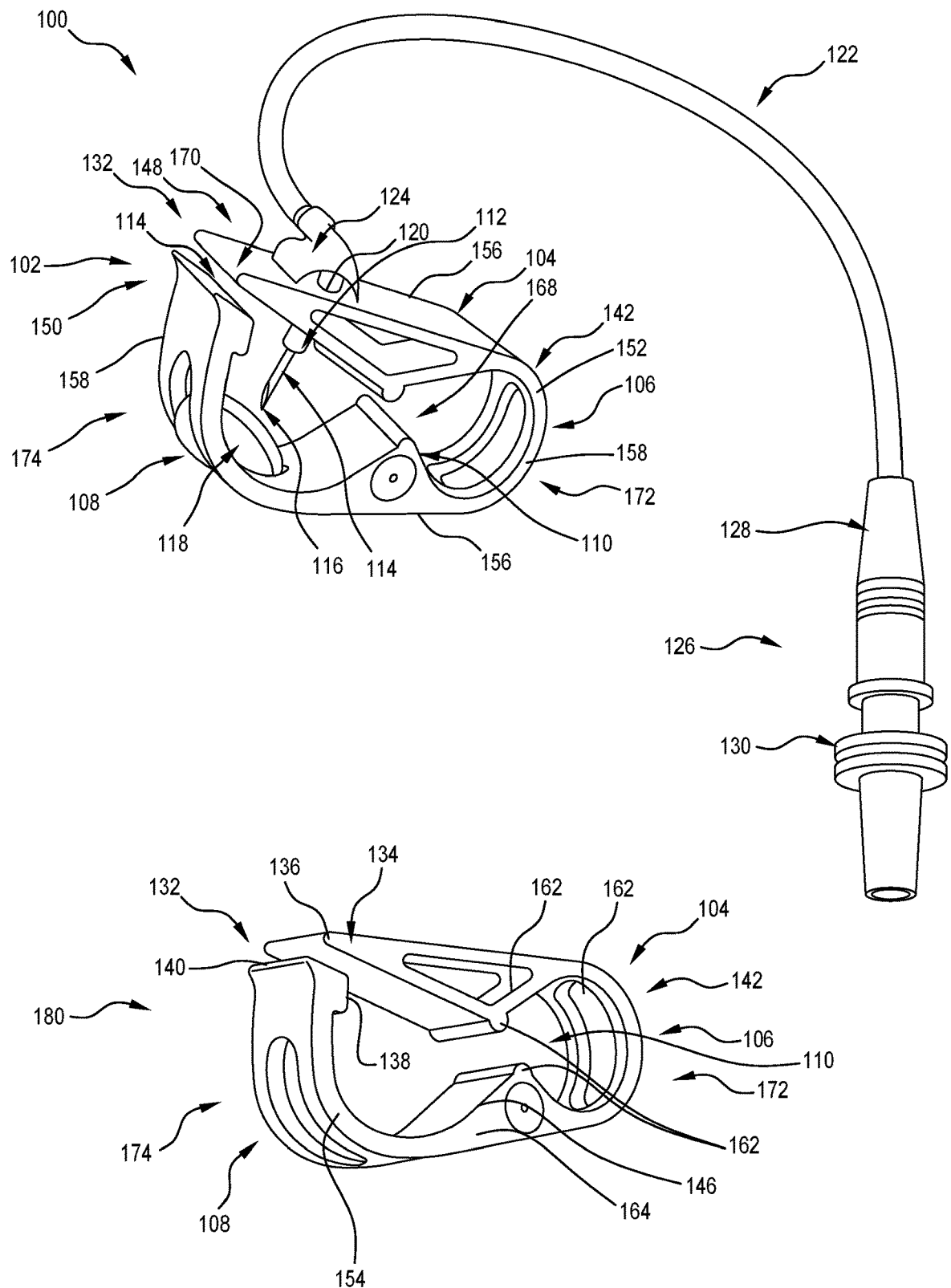
FIG. 2 is a photograph of one embodiment of a clip device according to the invention.

FIG. 2 shows one embodiment of a clip device 100 of the invention which, can be used to isolate the BSS infusion line 204, whilst penetrating the airline tubing 218 with a sharp self-retaining shaft 114 comprising a hollow internal lumen that can then be connected through bypass fluid line 122 to stopcock 210.

Clip device 100 comprises a first clip segment 102 comprising a fastener 104 for securing to air line 202, a pinch valve 110 for occluding air line 202 and a coupling 112 for connecting to air line 202. The coupling 112 is shown connected to bypass fluid line 122, which can be connected to stopcock 210.

Clip device 100 also comprises a second clip segment 180 comprising a pinch valve 110 for occluding the second fluid line 204. Apart from lacking the coupling 112 and associated elements, second clip segment 180 is identical or at least similar to first clip segment 102.

The fastener 104 comprises a proximal opening 106 and a distal opening 108 through which the respective fluid lines 202, 204 pass. Openings 106, 108 are sized to provide an interference fit so that they secure clip segments 100, 180 to fluid lines 202, 204. The proximal opening 106 and the distal opening 108 are disposed on opposing sides of clip segment 102, 180 with the proximal opening 106 being comprised at a proximal side 172 and the distal opening 108 being comprised at a distal side 174. The skilled person readily appreciates that the proximal side 172 and distal side 174 are so named for their orientation when deployed on infusion tubing 200. While the proximal side 172 is shown in FIG. 2 to be the side where the ratchet 132 is positioned, the positioning may be reversed.

The first and second clip segments 102, 180 comprise a tubing channel 168 extending between proximal opening 106 and distal opening 108. The pinch valve 110 is disposed within the channel 168.

The first clip segment 102 further comprise a bypass tube opening 120 through which the bypass fluid line 122 can extend. The bypass tube opening 120 may be disposed in or proximal to the rack 134 component of ratchet 132 on the distal side 174. The skilled person readily appreciates that the bypass tube opening 120 may be disposed in another part of clip 100 such as, the pawl 136 also on the distal side 174 or on the opposite side of the pinch valve 110 at the proximal side 172.

Coupling 112 may comprise a shaft 114 comprising a sharp point 116 to penetrate the first fluid line tubing wall 220 to communicate with the lumen and establish fluid communication between first fluid line 202 and shaft 114 of bypass fluid line 122. The coupling 112 may further comprise a coupling attachment 124 to connect the shaft 114 to the bypass fluid line 122. The bypass fluid line 122 may then be connected to the stopcock 210. The attachment to stopcock 210 is through fitting 128 which may comprise nipple 130. The bypass fluid line may comprise 23 gauge tubing. A skilled person will readily understand that tubing with other gauges may also be utilized such as, 25 gauge or 27 gauge.

The clip device 100 may further comprise a coupling guide 118 for positioning coupling 112 in an appropriate orientation to connect with the first fluid line 202. In the embodiment shown, coupling guide 118 comprises a raised block which provides a bias to coupling 112. As shown in FIG. 2, no bias is applied when the ratchet 132 is open and the bias is only applied when ratchet 132 is closed.

The clip device 100 can be closed and pinch valve 110 activated by engaging ratchet 132. Ratchet 132 comprises rack 134, comprising one or more tooth 136, and a pawl 138.

Pinch valve 110 is comprised of opposing stems 160 which are formed by rack end thickened segment 162 and pawl end thickened segment 164. Closing ratchet 132 brings stems 160 into close juxtaposition so that pinch valve 110 will occlude the fluid line on which it is disposed.

Clip device 100 further comprises a frame 142 which comprises an exterior surface 144 and an interior surface 146. Frame 142 may further comprise a shoulder 140 at a pawl end 150 to aid operation of ratchet 132 and surface texture 170 disposed on the exterior surface 144 at the rack end 148 which also aids user operation of ratchet 132 by providing some grip.

Frame 142 may comprise a looped shape. The looped shape may comprise, at the proximal side 172, a 180° curve between two stems 160. The 180° curve may provide the bias for the ratchet 132. The looped shape may further comprise a 90° curve between one stem 160 and pawl 138. When ratchet 132 is engaged or closed, the looped shape may comprise a continuous or closed loop and closed clip device 100 may comprise a general obround shape. When the ratchet 132 is disengaged or open, the looped shape may comprise an open loop.

Frame 142 comprises two long sections 156 and two short sections 158. The stems 160 are disposed on long sections 156. The proximal opening 106 and the distal opening 108 are comprised or substantially comprised on the short sections 158. In the embodiment shown proximal opening 106 is wholly located in a short section 158 while distal opening 108 is shown located partly in short section 158 and partly in long section 156. This positioning of distal opening advantageously provides an improved fitting onto the tube.

Figure 3:
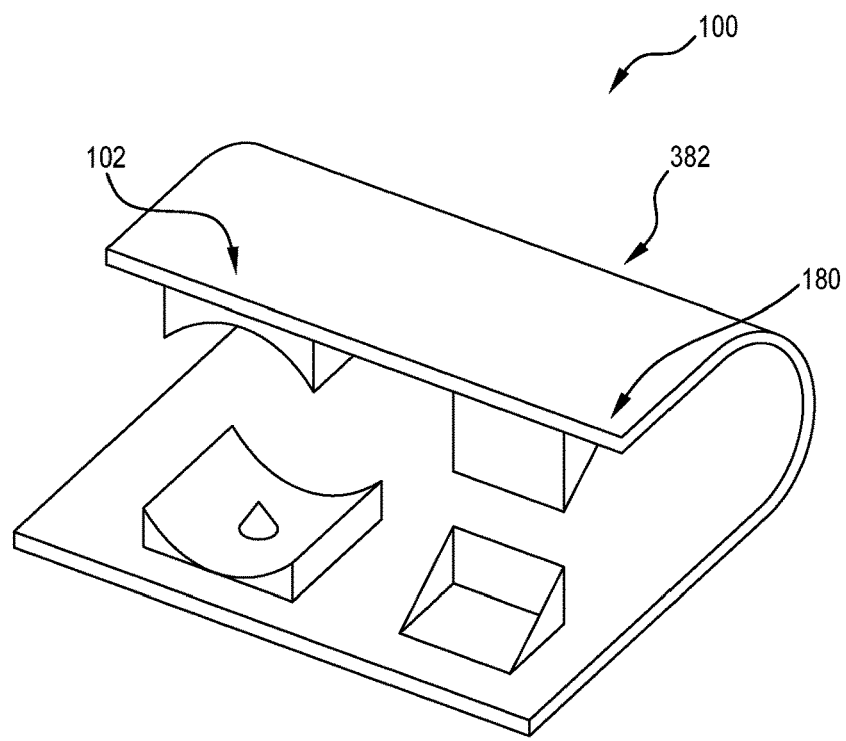
FIG. 3 is a drawing of another embodiment of a clip device according to the invention.
Figure 4:
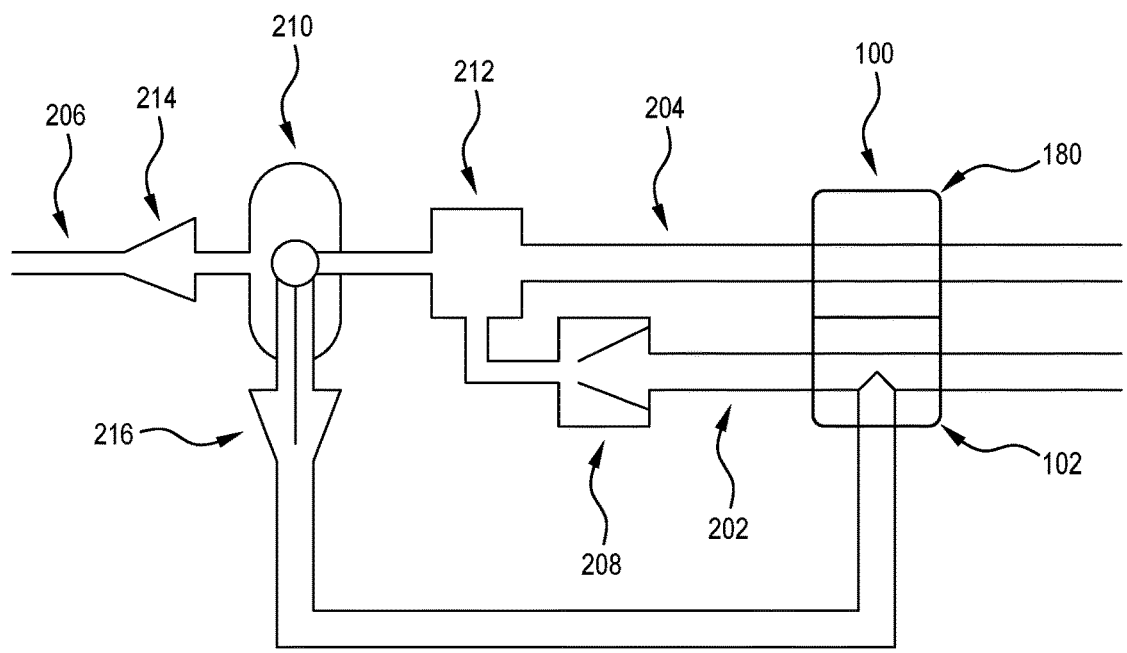
FIG. 4 is a drawing of the clip device of the invention deployed on the assembled infusion tubing used in the Constellation™ Vision System.

As will be evident from the above description and FIGS. 2 and 3, frame 142 provides the structure of the clip device 100 and defines the proximal opening 106, the distal opening 108, the first pinch valve 110, bypass tube opening 120, ratchet 132, shoulder 140, long sections 156, short sections 158, channel 168 and surface texture 170.

In another embodiment, the coupling guide may be an integral component of frame 142.

FIG. 3 shows another embodiment of a clip device 100 according to the invention, in which of first clip segment 102 and the second clip segment 180 are comprised on an integrated body 382. The integrated body 382 may comprise a central spine (not shown) which extends between the first segment 102 and the second segment 180. The central spine separates the channels 168 of the first clip segment 102 and the second clip segment 180. The integrated body 382 is of particular advantage because it allows simultaneous isolation of the first and second fluid lines 202, 204 with one easy attachment.

Another significant advantage of the present invention is that clip device 100 may be disposable.

The invention further provides a method for occluding two fluid lines and forming a connection comprising one of the fluid lines. The method comprises occluding a first fluid line with a first pinch valve disposed on a first clip segment; occluding a second fluid line with a second pinch valve disposed on a second clip segment; and connecting the first fluid line to a third fluid line with a bypass fluid line.

Prior to commencing an intraocular infusion, the clip device 100 can be activated and the stopcock 210 turned to close off the standard infusion line and thus open the communication between the bypass fluid line 122 and the ocular line 206 (see FIG. 3).

While the embodiment shown in the Figures and discussed above has infusion tubing 200 utilizing a three-way stopcock 210, any other suitable valve may be utilised.

The clip device 100 may be comprised of any suitable surgical grade material. In a preferable embodiment the clip device 100 is comprised of a surgical grade polymeric material such as one or more of a polyurethane; a polyamide; a fluoropolymer; a polyolefin; a polyvinylchloride, a polyimide; or a polyetheretherketone (PEEK). From the teachings herein a skilled person is readily able to select a suitable surgical grade material.

In this specification, the terms "comprises", "comprising" or similar terms are intended to mean a non-exclusive inclusion, such that an apparatus that comprises a list of elements does not include those elements solely, but may well include other elements not listed.

Throughout the specification the aim has been to describe the invention without limiting the invention to any one embodiment or specific collection of features. Persons skilled in the relevant art may realize variations from the specific embodiments that will nonetheless fall within the scope of the invention.

The invention claimed is:

1. A clip device for occluding two fluid lines and forming a fluid connection comprising one of the fluid lines, the clip device comprising:
    a first clip segment comprising a fastener for engaging to a first fluid line, a first pinch valve for occluding the first fluid line and a coupling for connecting to the first fluid line wherein the coupling comprises a shaft comprising a sharp point to penetrate the first fluid line tubing wall;
    a second clip segment comprising a second pinch valve for occluding a second fluid line; and
    a bypass fluid line connectable or connected to the coupling.

2. The clip device of claim 1 wherein the second clip segment also comprises a fastener for securing to the second fluid line.

3. The clip device of claim 1 wherein at least one of the clip segments comprise a proximal opening and a distal opening through which the respective first and/or second fluid line passes.

4. The clip device of claim 3 wherein the proximal opening and the distal opening are to be disposed on opposing sides of the segment.

5. The clip device of claim 1 wherein the first clip segment comprises a first tubing channel extending between the proximal opening and the distal opening.

6. The clip device of claim 5 wherein the first pinch valve is disposed within the first tubing channel.

7. The clip device of claim 1 wherein the second clip segment comprises a second tubing channel extending between a proximal opening and a distal opening.

8. The clip device of claim 1 wherein the second pinch valve is disposed within a second tubing channel.

9. The clip device of claim 1 wherein the first clip segment further comprises a bypass tube opening.

10. The clip device of claim 9 wherein the bypass tube opening is disposed in or proximal to a rack.

11. The clip device of claim 1 wherein the first clip segment and the second clip segment are comprised on an integrated body.

12. The clip device of claim 11 wherein the integrated body extends between the first clip segment and the second clip segment to separate channels of the first clip segment and the second clip segment.

13. The clip device of claim 11 wherein at least one of: the first clip segment, second clip segment and the integrated body, further comprise a ratchet for holding the clip device closed.

14. The clip device of claim 11 wherein at least one of: the first clip segment, second clip segment and the integrated body, comprise a frame, the frame comprising an exterior surface and an interior surface.

15. The clip device of claim 1 wherein the clip device further comprise a coupling guide for positioning the coupling in an orientation to connect with the first fluid line.

16. The clip device of claim 1 wherein the clip device is disposable.

17. A method for occluding two fluid lines and forming a connection comprising one of the fluid lines, the method comprising:
    occluding a first fluid line with a first pinch valve disposed on a first clip segment wherein the first pinch valve comprises a coupling, the coupling comprising a shaft comprising a sharp point to penetrate the first fluid line tubing wall;
    occluding a second fluid line with a second pinch valve disposed on a second clip segment; and
    connecting the first fluid line to a third fluid line with a bypass fluid line.

18. The method of claim 17 wherein the method comprises using a clip device comprising:
    the first clip segment comprising the fastener for engaging to a first fluid line, the first pinch valve for occluding the first fluid line and the coupling for connecting to the first fluid line;
    the second clip segment comprising the second pinch valve for occluding the second fluid line; and
    the bypass fluid line connectable or connected to the coupling.

19. A method of manufacturing a clip device for occluding two fluid lines and forming a fluid connection comprising one of the fluid lines, the method comprising:
    forming a first clip segment comprising a fastener for engaging to a first fluid line;
    a first pinch valve for occluding the first fluid line and a coupling for connecting to the first fluid line wherein the coupling comprises a shaft comprising a sharp point to penetrate the first fluid line tubing wall;
    forming a second clip segment comprising a second pinch valve for occluding a second fluid line; and
    forming a bypass fluid line connectable or connected to the coupling.

* * * * *